United States Patent [19]

Byers et al.

[11] Patent Number: 4,969,468
[45] Date of Patent: Nov. 13, 1990

[54] ELECTRODE ARRAY FOR USE IN CONNECTION WITH A LIVING BODY AND METHOD OF MANUFACTURE

[75] Inventors: Charles L. Byers, Canyon Country; Joseph H. Schulman, Granada Hills; David I. Whitmoyer, Los Angeles, all of Calif.

[73] Assignee: Alfred E. Mann Foundation for Scientific Research, Sylmar, Calif.

[21] Appl. No.: 300,859

[22] Filed: Jan. 24, 1989

Related U.S. Application Data

[63] Continuation of Ser. No. 875,334, Jun. 17, 1986, Pat. No. 4,837,049.

[51] Int. Cl.$^5$ .............................. A61B 5/04; B05D 5/12
[52] U.S. Cl. .................................... 128/642; 128/784; 29/829; 427/79; 427/96
[58] Field of Search ................................ 128/639–642, 128/644, 784; 427/79, 96, 99; 29/829

[56] References Cited

U.S. PATENT DOCUMENTS

| B 453,031 | 8/1973 | Fukase et al. | 156/3 |
| 3,755,704 | 8/1973 | Spindt et al. | 313/309 |
| 4,016,886 | 4/1977 | Doss et al. | 128/784 |
| 4,350,164 | 9/1982 | Allain, Jr. | 128/639 |
| 4,513,308 | 4/1985 | Green et al. | 357/55 |
| 4,551,149 | 11/1985 | Sciarra | 623/4 |
| 4,837,049 | 6/1989 | Byers et al. | 128/642 X |

FOREIGN PATENT DOCUMENTS

| 2555281 | 6/1977 | Fed. Rep. of Germany | 128/639 |
| 665890 | 6/1979 | U.S.S.R. | 128/642 |

OTHER PUBLICATIONS

Spindt et al., "Physical Properties . . . Cones", J. App. Phys., vol. 47, No. 12, p. 5428 et seq., Dec. 1976.
Prohaska et al., "A 16 Fold Semi-Microelectrode . . . ", Electroenceph and Clin. Neuro, 1979, 47, p. 629, 631.
Wise et al., "An Integrated Circuit . . . ", IEEE Trans BioMed. Eng., p. 238 et seq., vol. BME 17, No. 3, Jul. 1920.
"Multichannel Multiplexed . . . Arrays", Neural Prothesis Program, U. of Mich., Oct. 1987.
Guyton et al., "Theory . . . Chronic Stimulation", Med. and Biol. Eng., vol. 12, No. 5, Sep. 1974, p. 613–620.
Wise et al., "A Low Capacitance Multi Electrode . . . " IEEE Trans. Bio Med. Eng., vol. 22, No. 3, p. 212–219, May 1975.
Klomp et al., "Fabrication of Large Arrays . . .", J. Bio Material Res., vol. 11, p. 347–64, 1977.
White, "Integrated Circuits . . . Arrays", 1st Conf. on Elect. Stim . . . , p. 199–207, 1974.
Am. J. of Physiology, 212(5), pp. 1209–14, 1967, P. V. Malven et al.
Brain Research, 142, pp. 363–367, 1978, H. F. Carrer et al.
Ko, "Solid-State . . . Research", IEEE Trans Bio Med Eng., p. 153–160, vol. 13, No. 2, Feb. 1986.

*Primary Examiner*—Lee S. Cohen
*Attorney, Agent, or Firm*—Robert R. Meads

[57] ABSTRACT

The electrode array is a device for making multiple electrical contacts with cellular tissue or organs. The electrode array includes a base (1), a two dimensional array of conducting protuberances (2) arising from the base and serving as electrodes, and conductors (3) embedded onto the base and connected to such protuberances for transmitting electrical signals to and/or from the protuberances. The protuberances may also include an insulating layer (15) which covers either the entire protuberance or which leaves the tips exposed for making focused electrical contact. Electrode arrays may be used used singly or in combination with a second electrode array so as to form a sandwich around a target tissue. The sandwich electrode array (16, 17) may employ indexing cones for aligning the opposing electrode arrays and for limiting their vertical proximity. The conductors of the electrode array may be electronically connected or coupled to processing circuitry which amplifies and analyzes the signal received from the tissue and/or which generates signals which are sent to the target tissue and possibly coordinates the generated signals with signals which originate with the tissue.

20 Claims, 7 Drawing Sheets

ELECTRODE ARRAY FOR USE IN CONNECTION WITH A LIVING BODY AND METHOD OF MANUFACTURE

RELATED APPLICATION

This application is a continuation of U.S. Application Ser. No. 875,334, filed June 17, 1986, now U.S. Pat. No. 4,837,049, whose disclosure is, by reference, incorporated herein.

BACKGROUND

The invention relates to electrodes employed for electrically sensing or stimulating biological tissues. In particular, the invention relates to two dimensional electrode arrays and to methods for making and using such electrode arrays. The electrode array is particularly useful for making multiple electrical contacts at the cellular level, for electronically discriminating amongst individual cells or small groups of cells within a tissue or organ, and for directing electrical signals to or from such individual cells or small groups of cells within such tissue or organ, especially neural tissues and organs.

A nerve is a cordlike structure which is composed of numerous nerve fibers conveying impulses between a part of the central nervous system and some other region of the body. A nerve is made up of individual nerve fibers with their sheaths and supporting cells, small blood vessels, and a surrounding connective tissue sheath. Each nerve fiber is surrounded by a cellular sheath (neurilemma) from which it may or may not be separated by a laminated lipo-protein layer (myelin sheath). A group of such nerve fibers surrounded by a sheet of connective tissue (perineurium) is called a fasciculus. The fasciculi are then bound together by a thick layer of connective tissue (epineurium) to form the nerve.

Neurologists have long sought an electrode device which could establish stable electrical contact with a large number of individual nerve fibers within a nerve. Such a device would find wide medical application for sensing neurological impulses, facilitating the analysis and interpretation of such impulses, and delivering electrical stimuli to target nerve fibers as a reaction to such analysis or as a result of external input. The ideal electrode device would be adapted to the anatomy of the nerve so that it could penetrate the nerve in a nondestructive fashion in order to form focused electrical contacts with a very large number of individual nerve fibers.

Nerve cuff electrodes are employed in the neurological sciences for sensing nervous impulses and for electrically stimulating nerves The nerve cuff electrode encircles the entire nerve and senses gross nervous impulses arising from the nerve fibers within the nerve. The nerve cuff electrode may also be employed to electrically stimulate the nerve. Individual nerve fibers within a nerve may be functionally distinct from the other nerve fibers. The utility of the nerve cuff electrode is limited by its inability to specifically direct signals to or from selected nerve fibers within the nerve.

In order to make electrical contact with individual nerve fibers within a nerve, narrow gauge needle electrodes may be employed. When a narrow gauge needle is inserted into the nerve, there is a chance that it may make electrical contact with an individual nerve fiber or a small number of such fibers. If electrical contact is desired with each of several nerve fibers, then several needle electrodes must be employed. However, the technique of using multiple needle electrodes becomes progressively more and more difficult as the number of electrodes increases. Hence, there is a limit to the number of needle electrodes which can be usefully employed on a single nerve. Also, the electrical contact between a needle electrode and its corresponding nerve fiber can be disrupted by muscle motion and other forms of motion, since the end of the needle opposite the electrode extends outside the nerve and can be levered by relative motion of neighboring tissues. Therefore, long term implantation of needle electrodes with stable electrical contact with nerve fibers is not possible with prior art needle electrodes.

An electrode array having several electrodes integrated into one device is disclosed by Robert L. White. (Proceedings of the first International Conference on Electrical Stimulation of the Acoustic Nerve as a Treatment for Profound Sensorineural Deafness in Man, published by Velo-Bind, Inc. (1974), edited by Michael M. Merzenich, et al., chapter entitled "Integrated Circuits and Multiple Electrode Arrays," pp. 199-207, by Robert L. White) White's electrode array employs a prong shaped base fabricated from a silicon wafer. The silicon base supports an array of electrodes which are deposited thereon toward the end of the prong. Each of the electrodes is small, flat, and circular, about 50 micrometers in diameter. Each electrode is connected to a corresponding conductor which carries signals to and from the electrode. The conductor is electrically insulated from the tissue by a layer of silicon dioxide. In use, the prong is inserted tip first into neural tissue. Neural tissue is displaced by the prong as it is inserted. Substantial damage to neural tissue can result from the insertion process due to the relatively large bulk of the prong. Since neural tissue slides tangentially past the electrodes during the insertion process, the flatness of the electrodes helps to minimize the resultant disruption and destruction of neural tissue. However, once the device is inserted, the flatness of the electrodes limits the contact between the electrode and the neural tissue. Flat electrodes can make electrical contact only with neural tissue which is directly adjacent to the surface of the prong.

Multiple electrode devices with micro electrode tips protruding beyond and in a plane parallel to a silicon carrier (i.e. planar electrodes) are disclosed by Wise et al. (IEEE Transactions on Biomedical Engineering, Vol. BME-17(3), pp 238-247, July 1970, "An Integrated Circuit Approach to Extracellular Microelectrodes," and Vol. BME-22(3), May 1975, "A Low-Capacitance Multielectrode Probe for Use in Extracellular Neurophysiology") and by Ko (IEEE Transactions on Biomedical Engineering, Vol. BME-33, pp 153-162 (Feb. 1986), "Solid State Physical Transducers for Biomedical Research"). Wise et al. teach that the lateral spacing and length of the protruding tips may be controlled to produce various planar electrode arrays. Like the White device, the silicon carrier of the Wise et al. and Ko devices have the shape of a prong and may cause significant tissue damage to the nerve during the insertion process. Also, if the Wise et al. and Ko prong-shaped devices are implanted, their large bulk compromises the stability of the electrical contact between the electrode tips and individual target cells. Additionally, the thinness of the prong can make it susceptible to shear damage with side loading. Further, since the silicon carrier and the electrode tips are essentially coplanar with the tips cantilevered freely beyond the end of the carrier, the carrier imparts little if any transverse stability to the fragile tips during insertion of the Wise et al. and Ko prong-shaped devices or after their implantation. Moreover, the number of useful electrodes which may be incorporated into the Wise et al. and Ko devices is inherently limited. Moreover, since the electrode tips are aligned in a row along the edge of the silicon carrier, it is not possible to array the electrodes into a configuration with more than one dimension.

Thus, what is missing from the prior art and what is needed by practicing neurologists is an implantable electrode device which can electrically contact a large number of individual cells within an organ or tissue for sensing and controlling various bodily functions. The individual contacts should each be focused within a small region so that they involve single cells only. However, the range of the contacts should extend over a relatively large two or three dimensional region within the organ or tissue. The electrodes of the device should make positive contact with target cells and should be electrically stable over long periods of time, even with recurrent movement in adjacent tissues. On the other hand, the device should be able to penetrate the target organ without being intrusive so that tissue damage to the target organ is minimal. The device should have a small volume and a robust construction for practical medical applications.

SUMMARY

The electrode array of the present invention is a device for establishing stable electrical contact with biological tissues. In the preferred embodiment, the electrode array has a configuration for making multiple extracellular contacts and for conducting electrical signals to or from each cell with which there is contact. However, the electrode array can also be employed for measuring the voltage potential of the surface of organs and tissues, e.g. for EKG or EEG.

The electrode array includes a base of semiconducting or nonconducting material having a support surface, a two dimensional array of conducting protuberances which extend substantially perpendicular to and from the support surface of the base and serve as electrodes, and conductors incorporated onto or in the base and connected to the protuberances for carrying electrical signals to and/or from such protuberances. The invention also includes various embodiments of the electrode array and methods for using and fabricating such electrode arrays.

In a preferred embodiment of the electrode array, the protuberances are coated with an insulating layer of dielectric material, except for their tips. This feature narrows and focuses the contact area of each protuberance to a relatively small region and facilitates the ability of the protuberance to contact single cells or small groups of cells. The average number of extracellular contacts per protuberance may be adjusted to one by adapting shape and height of the protuberances and the exposed surface area of the tips.

In an alternative embodiment, the electrode array is capacitive. In this embodiment, the entire length of the protuberances, including the tip, is covered with an insulating dielectric. Hence, each protuberance makes capacitive contact with cellular tissue.

In yet another embodiment which is particularly well adapted for establishing multiple electrical contacts with a large number of nerve fibers, a combination of two electrode arrays are employed to form a sandwich on either side of a nerve or target organ. The two electrode arrays are situated on opposing sides of the nerve with the protuberances facing toward the center. The two electrode arrays are then brought closer together until they both contact the nerve and the protuberances penetrate into the nerve for making electrical contact with individual nerve fibers. At this point the electrode arrays are joined together as for example by intermeshing protuberances from the arrays. The combination electrode array is then supported by the nerve to which it is clamped. Since electrical contact is made on both sides of the nerve, the sandwich electrode array will make approximately twice the number of electrical contacts as compared to a single electrode array. Also, electrical contact between the electrode array and the nerve is enhanced by the fact that the electrode array is supported by the nerve to which it is attached. Each of the electrode arrays within the sandwich may be either the conductive type or the capacitive type.

The invention also includes various biomedical applications for the different embodiments of the electrode array. The electrode array may be either implanted or attached to skin. An electrode array may be employed for measuring the voltage potential of individual cells or of the surface area of an organ. However, in the preferred application, the electrode array is surgically implanted for establishing long term electrical contact with multiple cellular elements of an internal organ or tissue. The implanted electrode array may either electrically stimulate individual cells within the target organ or may sense nervous impulses within individual cells. Under some circumstances, the electrode array may both sense and stimulate electrical activity. Also, the electrical activity may be amplified and/or analyzed. And finally, the stimuli may be electronically correlated with the activity of the target cells. Because the two dimensional array greatly increases the number of protuberance which may be incorporated into a single device, the complexity and redundancy of the protuberances is greatly enhanced. Consequently, it is possible to establish multiple electrical contacts with relatively complex biological systems.

The invention also includes various special procedures employed for the fabrication and subsequent use of the electrode array. Since several electrode arrays may be fabricated on a single wafer, it is useful to employ indexing cones which mark out the various electrode arrays. The indexing cones can have a shape which is similar to the protuberances, but are greater in height. After the electrode arrays have been deposited onto the wafer and the various subsequent steps have been completed, the indexing cones may be used as an index for guiding the sawing of the wafer into separate base pieces. The indexing cones may also be employed with the sandwich electrode array for aligning the two electrode arrays with one another and for controlling and limiting the proximity of opposing electrode arrays so as to avoid damaging the sandwiched nerve by exerting excessive pressure.

DETAILED DESCRIPTION OF THE INVENTION

The invention is an electrode array which is to be applied to body tissue to provide an effective electrical connection therewith, whether for sensing or stimulating purposes. The electrode array provides a multiple possibility of successful electrical contact, and is intended to cause minimal damage to the body tissue or upset to the body system. The electrode array includes an array of conductive protuberances which serve as electrodes. The protuberances arise from a base and are connected by electrical conductors to terminals on the base. The terminals and conductors may be employed to connect individual protuberances or groups of protuberances of the electrode array to other electrical circuits.

If the electrode array is to be used for sensing low voltage body signals, an amplifier would likely be the first electrical circuit connected to the protuberances and/or terminals. Then, of course, the signals (information) may go on to be handled by analog or digital electronic methods and may involve transmission, multiplexing, filtering, data processing or other known electronic techniques. The particular use would determine the particular other electrical circuits to be used.

If the electrode array is to be used for electrically stimulating a tissue, the terminals would be connected to circuits which provide the output for the stimulation signals. The conductors would then carry these stimulation signals from the terminals to the corresponding protuberances.

Figure 1:
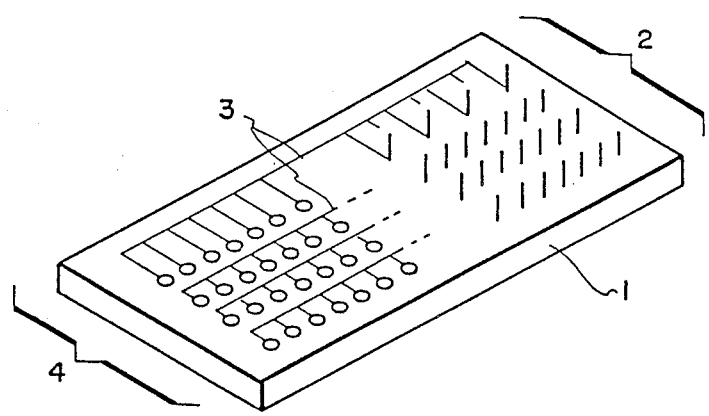
FIG. 1 is a perspective view of one embodiment of the electrode array illustrating a semiconductor base, an array sharp protuberances arising from the base, and corresponding terminals. The array of sharp protuberances illustrate the concept of "bed of nails."

FIG. 1 is a perspective view illustrating the concept of a "bed of nails," showing the protuberances and terminals. It is drawn to illustrate the concept of a base (1) having a support surface with protuberances (2) arising substantially normal therefrom with conductors (3) leading from the protuberances (2) to terminals (4). The terminals illustrated in FIG. 1 are bonding pads.

Figure 2:
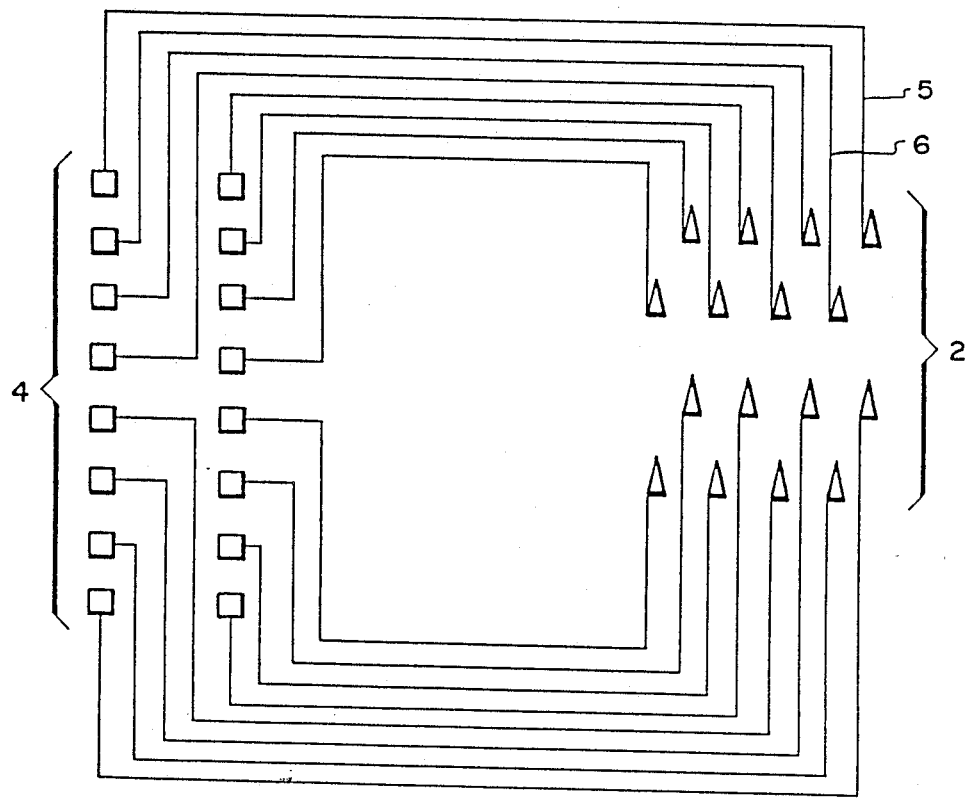
FIG. 2 is a schematic diagram of the electrode array of FIG. 1 illustrating the path of the individual conductors which electrically connect each protuberance to a corresponding terminal or bonding pad.

FIG. 2 is a more detailed view of FIG. 1 and illustrates the concept of connecting an array of protuberances (2) to an array of terminals (4) by means of conductors (e.g. 5 and 6).

Figure 3:
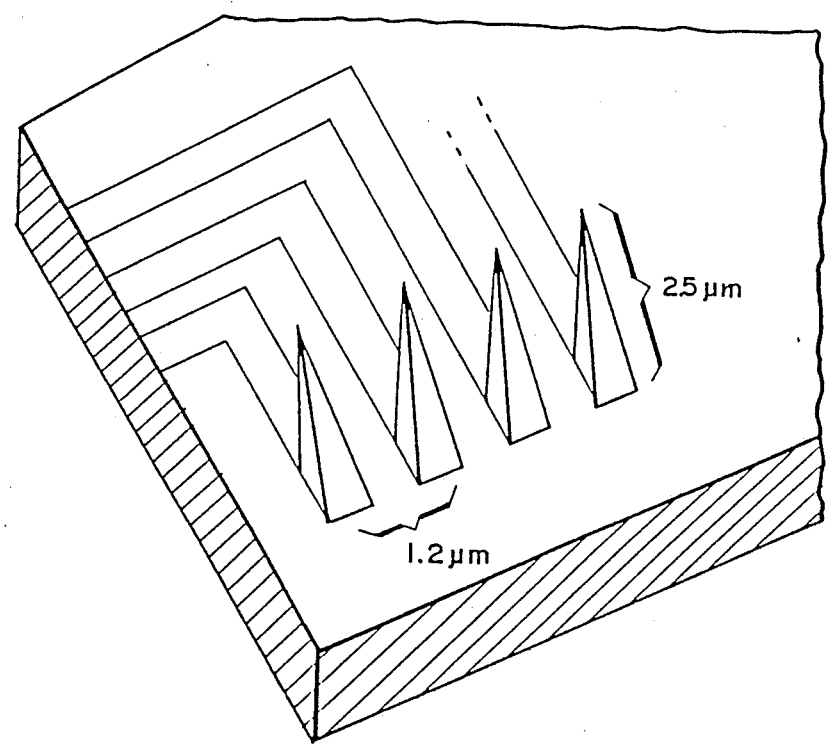
FIG. 3 is an enlarged view of a fragment of the electrode array of FIG. 1, illustrating the pyramidal shape of the protuberances and indicating typical dimensions for the height of the protuberances and the distance between adjacent protuberances.

FIG. 3 is a view of an array of protuberances in the shape of pyramids, illustrating the dimensions which may be involved. The protuberances, or needles, may, of course, be taller and narrower. Spacing may vary, as may the size of the protuberances. Of course, such protuberances may be conical or other elongated shapes.

Figure 4:
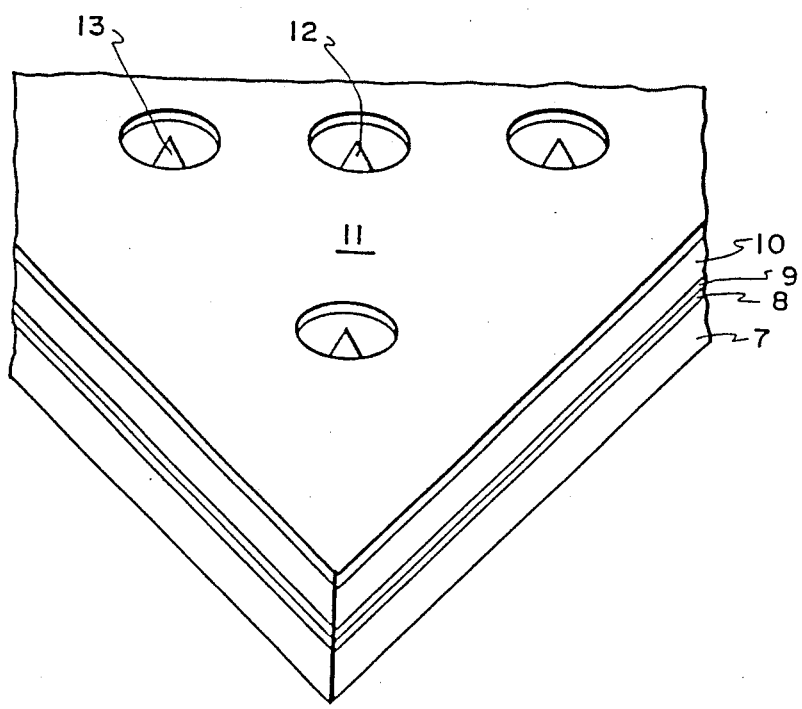
FIG. 4 is a perspective view of a section of an alternative embodiment of the electrode array having conical protuberances illustrating a deposition mask attached to a metallic film atop the base for growing the conical protuberances.

FIG. 4 illustrates protuberances being grown through a mask onto a metallic film (9). The protuberances shown in FIG. 4 have the shape of cones or needles. Below the mask lies a sandwich which includes a silicon base (7), an insulation layer of silicon dioxide (8), and the metallic layer (9) upon which the protuberances are being grown. Above the metal layer (9) is a spacing layer (10). The spacing layer (10) may have a composition of silicon dioxide, photoresist, or other material. The spacing layer (10) is not required for all applications. Atop the spacing layer (10) is a the top mask or fine mesh screen (11). After the protuberances are completely grown, the mask is carefully removed, leaving the protuberances atop the metallic layer (9). The conductors are subsequently formed from the metallic layer (9).

Figure 5:
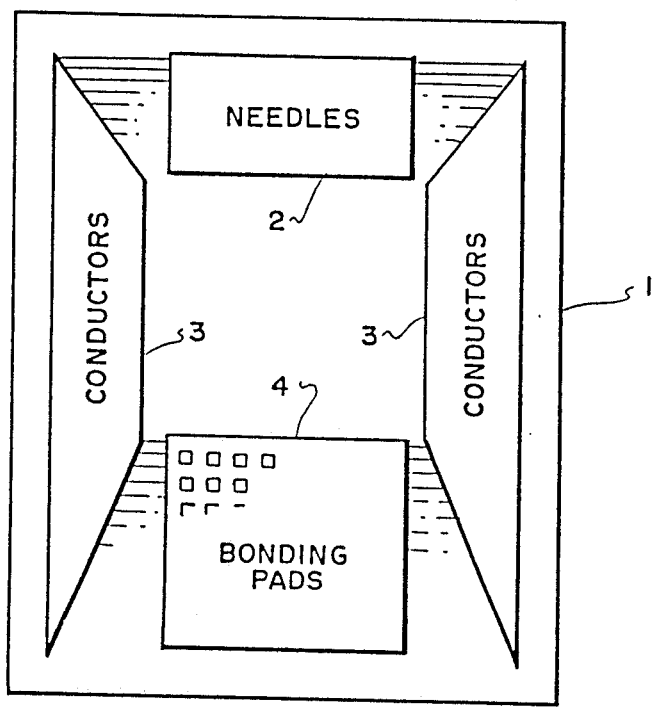
FIG. 5 is a further schematic diagram of the electrode array of FIG. 1 illustrating the layout of the protuberances, terminals, and conductor.

FIG. 5 shows a schematic layout for an electrode array. An array of protuberances arise from a base (1) and are connected by electrical conductors (3) to bonding pads (4).

Figure 6:
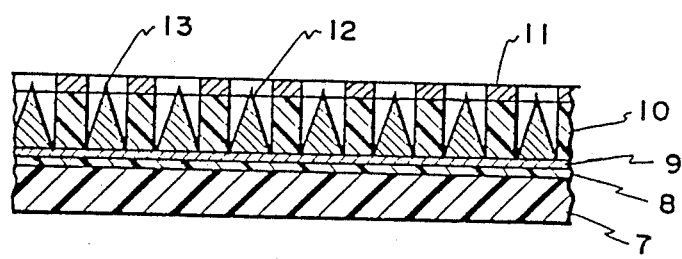
FIG. 6 is a sectional view of the electrode array of FIG. 4 illustrating the relationship between the conical protuberances and the deposition mask.

FIG. 6 is a cross-section of a deposition mask (11), showing the cones having been deposited through the holes of the mask. The cones (e.g. 12 and 13) are shown atop metallic layer (9). The underlying insulating layer (8) and base or substrate (7) are also shown.

Figure 7:
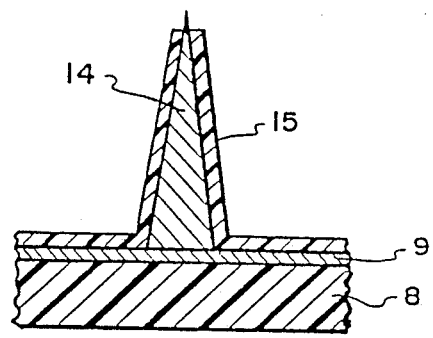
FIG. 7 is sectional view of an alternative embodiment of the electrode array illustrating a protuberance having a dielectric coat covering the protuberance, exclusive of the tip.

FIG. 7 is an illustration of a needle protuberance (14) covered with an insulating layer of dielectric (15), e.g. silicon dioxide. The tips of the needle protuberances are left exposed and uncovered by dielectric (15). Below the protuberance (14) is metallic layer (9) upon which the conductors are formed. The underlying insulation layer of dielectric (8), e.g. silicon dioxide, is also shown The underlying base is not shown.

Figure 8:
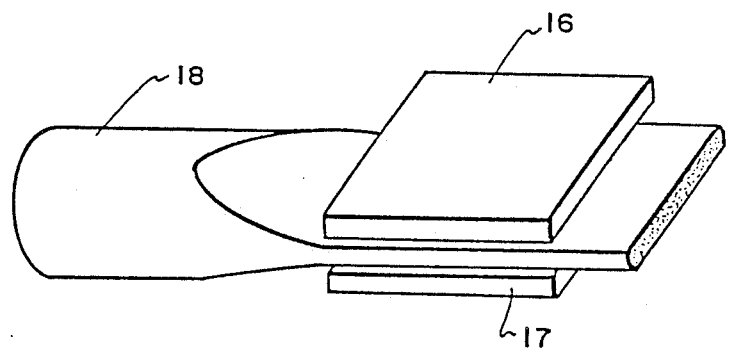
FIG. 8 is a perspective view of two electrode arrays forming a sandwich on either side of a flattened nerve.

FIG. 8 is an illustration of a combination of two electrode arrays (16 and 17) disposed on a single nerve (18) to form a sandwich electrode array or combination electrode array. The nerve is shown simply flattened although it may be further prepared to receive a sandwich electrode array by removal of a portion of its sheath and/or surrounding structures. The bonding pads or terminal portion of the electrode array may overhang from the nerve so as to clear the nerve in order to permit the bonding pads or terminals to be connected to external circuits. In one embodiment of the electrode array, the bonding pads or terminals are located on the edge of the base so as to facilitate the connection between the electrode array and external circuits.

Electrode arrays may be employed for measuring the voltage potential of the skin surface, e.g. for electrocardiograph and electroencephalograph measurements. In such applications, the electrode array may either penetrate the skin or may be applied more lightly. By penetrating the skin, a better connection is obtained without the use of conductive ointments. In addition, a capacitive coupling may be obtained by having the protuberances entirely covered with a passivating layer (dielectric) and applied to penetrate the skin. Thus, if the protuberances are electrically joined, the surface areas of the protuberances become one capacitive plate of substantial area and the dielectric lies between such plate and the other plate of the capacitor, viz. the surface of the skin or body tissue which is being measured.

Figure 9:
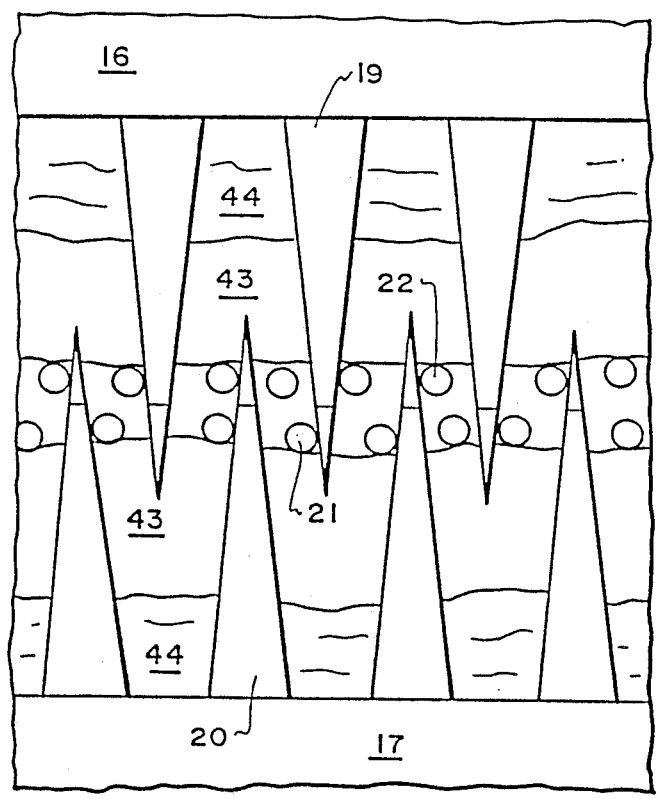
FIG. 9 is a sectional view of the two electrode arrays of FIG. 8 illustrating interdigitated protuberances penetrating a nerve from opposite sides and electrically contacting individual nerve cells.

FIG. 9 is a cross-section of a nerve and shows interdigitated needle shaped protuberances as might occur from the arrangement shown in FIG. 8. The interdigitated needles (e.g. 19 and 20) are shown penetrating a nerve from opposite sides and contacting or coming into near proximity to the myelinated or unmyelinated fibers (21 and 22). The needles are shown penetrating the perineurial sheath (43) and the extraperineurial tissue (44). Some of such tissue may be removed in preparation for the application of the electrode arrays. It is noted that the needles are shown as exposed only at their tips or ends. Such structure is particularly useful in sensing, in order to limit the sensed electrical activity to a single fiber or a few fibers. A larger portion of the needle may be exposed in stimulating situations. In order to enhance the likelihood of successfully sensing or stimulating a particular nerve fiber within a particular type of nerve, the dimensions, needle length, exposed tip length, amount of interdigitation, and needle spacing of the electrode array may be adapted to the anatomy of such nerve.

Figure 10:
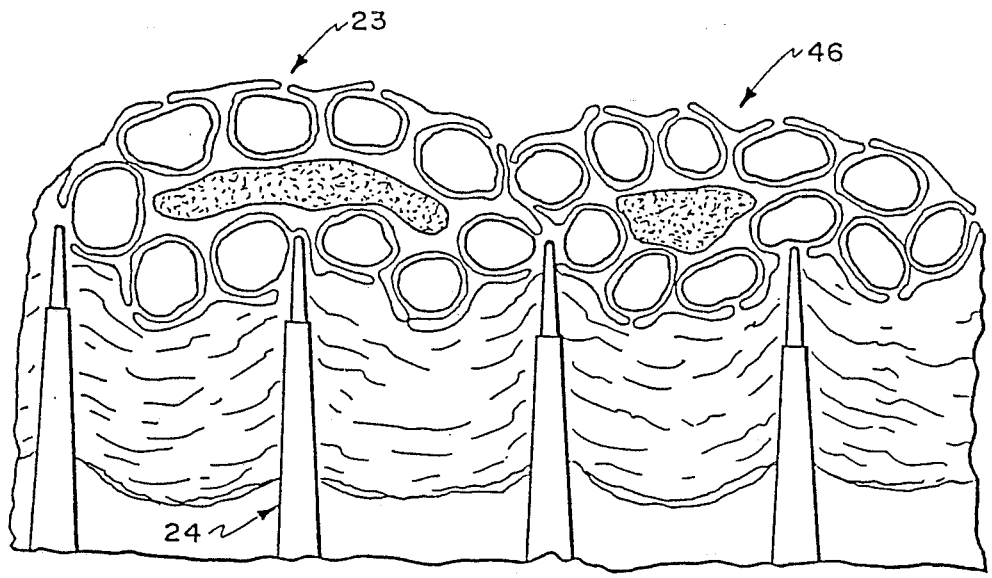
FIG. 10 is a sectional view of Schwann cells enveloping unmyelinated nerve fibers illustrating the conductive tip of a protuberance from an electrode array lying in close proximity to a nerve fiber.

FIG. 10 shows Schwann cell structures (23 and 46) disposed around "C" class nerve fibers, such as (25). A needle shaped protuberance (24) is shown in close proximity to nerve fiber (25).

Figure 11:
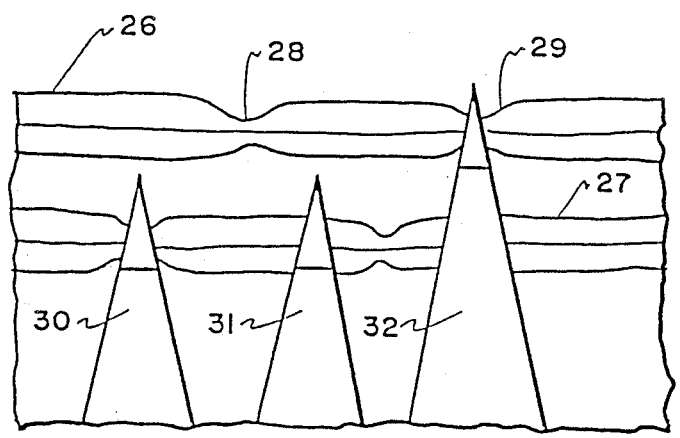
FIG. 11 is a sectional view of two myelinated nerve fibers having nodes of Ranvier illustrating the conductive tips of protuberances of differing heights from an electrode array lying in close proximity to said nodes.

FIG. 11 shows two nerve fibers (26 and 27), their nodes of Ranvier (28 and 29), and needles (30, 31, and 32) penetrating into the nerve Needles (30 and 32) are in proximity to said nodes and would more likely pick up electrical signals than would needle (31).

Figure 12:
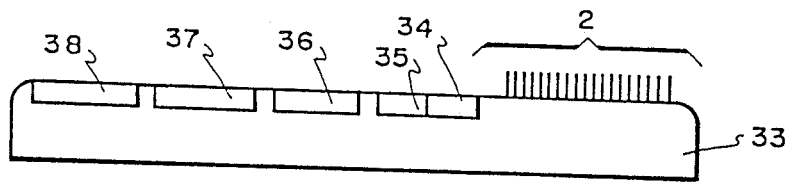
FIG. 12 is a side plane view of an alternative embodiment of the electrode array having a monolithic base structure, protuberances, and several electronic devices.

FIG. 12 illustrates a monolithic base structure (33) in which several active electronic devices (34, 35, 36, 37, and 38) are created and on which are created the protuberances (2), for penetrating the body tissue.

Figure 13:
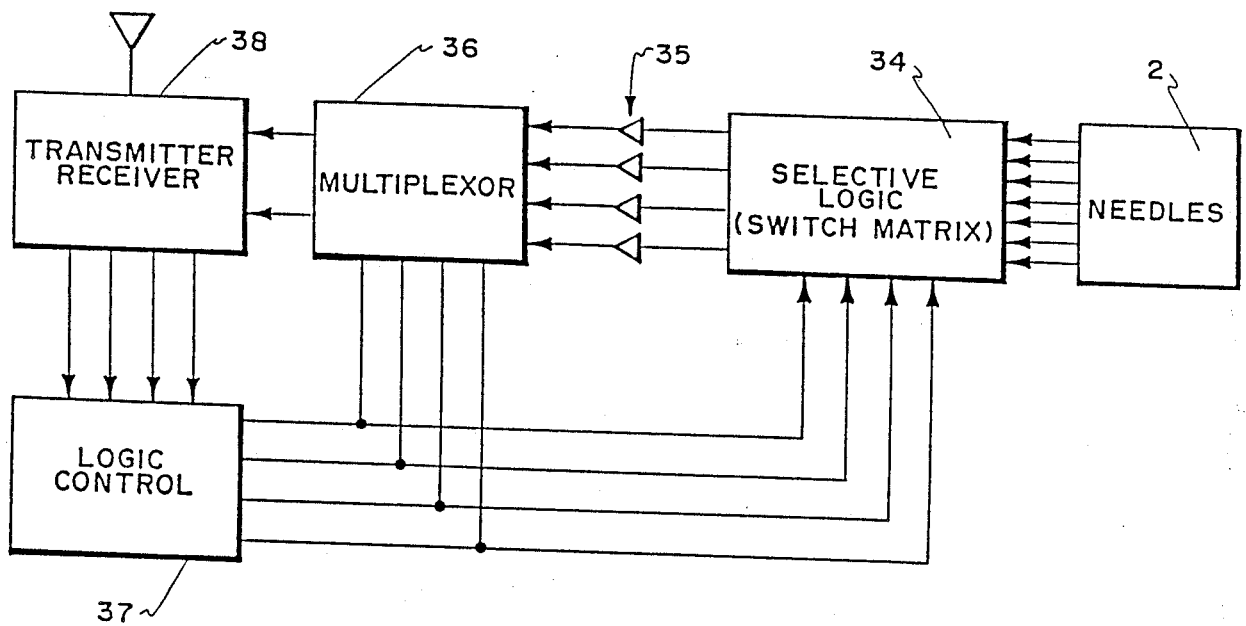
FIG. 13 is schematic diagram of the electrode array of FIG. 12 illustrating the interconnections for outputting the signal of the protuberances. Included are a transmitter and receiver for transmitting signals between the protuberances and an external unit.

FIG. 13 shows the interconnected electronic devices for switching the output of a sensory device. The transmitter and receiver (38) are shown, for transmitting the sensed information and receiving information for controlling the multiplexor (36) and the selective logic (34) of the sensing needles, or protuberances. Logic control (37) provides control over the multiplexor (36) and selective logic (34). In this manner external control may be exercised in order to select particular needles which are in suitable contact, or proximity, to desired nerve fibers. Amplifiers (35) provide increased signal strength. Integrated circuit technology may be used to provide the desired interconnections. Further, it may be appreciated that the transmitter and receiver (38) may be other than radio frequency. Then may transmit and receive utilizing infrared, magnetic induction, reflected impedance, acoustic waves, volumetric conduction or any other suitable well-known means for transmitting and receiving information. Such transmitter and receiver may be powered from inside or outside of the body. The entire implanted electrode array may be powered from outside the body by power transferred into the body through the receiver. In this manner, one or more electrode arrays could be coordinated to operate together or in response to one another. An electrode array implanted in the brain could, without any wires (tetherless), communicate and control an electrode array attached to a muscle, a nerve or other body part. An electrode array or several electrode arrays attached to the motor cortex of the brain could transmit, in tetherless fashion, many channels of information to receiving body parts, such as muscles, to which electrode arrays are attached.

Figure 14:
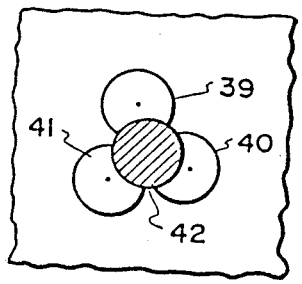
FIG. 14 is a sectional view of the fragment of two electrode arrays shown in FIG. 15 indicating the relative position of the opposing indexing cones.

FIG. 14 illustrates indexing cones or aligning means Three indexing cones (39, 40, and 41) arise from a first base piece which a single crosshatched indexing cone (42) descending from a second opposing base piece. The indexing cones from the first and second base pieces intermesh. The crosshatched cone (42) may register and align a mask, cover or other item which overlies the second base piece.

Figure 15:
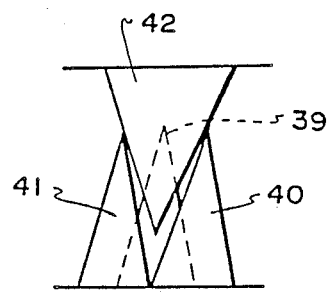
FIG. 15 is a plane view of indexing cones from two opposing electrode arrays illustrating the aligning and vertical positioning of the two electrode arrays by means of the indexing cones.

FIG. 15 shows a side view of the indexing cones of FIG. 14 and illustrates how such indexing cones intermesh so as to index or align two devices. Two or more of such groups of indexing cones would be used in accomplishing the registration. It is not believed alignment was been achieved previously using such microstructures. In the preferred use of the invention, the electrode array is connected to a nerve A nerve is generally of linear shape, but does not ordinarily lie in a straight line. Considering the needles of the array to be longitudinally disposed along the direction of the nerve, one or more needles along such longitudinal direction may make contact with the same or different nerve fibers. The needles most likely to be useful are those which touch or are in close proximity to the desired fibers. Laterally spaced needles may also be found to have made contact with the same nerve fiber. Other laterally spaced needles may connect to nearby nerve fibers which may have the same or different signals. Reinforcement of the sensing of signals can thus be obtained. Similarly, reinforcement of stimulation signals can thus be provided. From the explanation provided above, it can be seen that sensing or stimulation of the same or different nerve fibers is possible.

The smallest class of nerve fibers are unmyelinated "C" fibers. Adjacent fibers of this class appear, from our own observation, to be spaced from approximately $\frac{1}{2}$ micrometer to 5 micrometers apart, center to center. Larger nerve fibers, e g "A" and "B" fibers, which are usually myelinated (surrounded by a sheath) appear to be spaced approximately 10 micrometers to 50 micrometers from adjacent fibers. In addition, a thickness of connective tissue encloses all of the component fibers in a nerve. In order to penetrate the nerve or in order to enter the fiber bundle sufficientlY, but not too much, the needles would be approximately ½ micrometer high to on the order of 100 micrometers high. In selecting the correct needle height, consideration has to be given to the sheaths, Schwann cells, and other tissue to be penetrated in order to contact the nerve fiber. Similarly, for other tissues, the depth of penetration desired would determine the height of the needles. If the needles are fabricated with optimal materials and geometry within the above described dimensions, emphasizing a small tip radius, narrow taper, spacing and length appropriate to the tissue involved, the likelihood of making electrical contact with a minimum of tissue damage is high.

Depending on the capability of creating long needles, it is desired to have them as long and narrow as possible. Aspect ratios (height to base) of 10 to 1 are readily achievable. A needle which is 100 micrometers high might have a base of from 5 micrometers to 10 micrometers in diameter or greater.

It should be appreciated that the small size of the needles minimizes the likelihood that nerves, organs, tissue, or other body parts would be damaged by application of the electrode array and penetration by the needles.

The spacing of the needles, transversely across a nerve, would be from approximately ½ micron to on the order of 100 micrometers. "On the order of" means, in this context, and as used herein, within the range of 1/10 of the dimension to 10 times the dimension. Spacing of the needles along the length of a nerve might well be greater than the lateral spacing of the needles across the nerve. That is, the spacing distance between needles along the length of a nerve can vary a great deal. Needles or groups of needles might well be longitudinally spaced 1000 micrometers, 2000 micrometers, etc., from one another, depending on the desired density of electrical contact with the nerve.

The needles (electrodes) must, therefore, be spaced having in mind the specific application. The needles should be small and sharp enough to avoid damaging the nerve. Also the electrically conductive portion of each needle should be small enough to contact only a single fiber and thereby obtain signals from only one fiber. Consequently, a preferred embodiment of the invention is to insulate the needles, except at or near their tips so that only a small electrically conductive portion of each needle is exposed. In this way, each needle is less likely to electrically contact more than one fiber.

In addition, the needles must be high or long enough to assure sufficient penetration of the desired nerve so as to make electrical connection with the nerve fiber inside the nerve. In order to reach the nerve fiber, the sheath and other connective tissues must be penetrated. However, "electrical connection" or "contact" with a nerve fiber or other body tissue may mean actual physical contact with the nerve fiber or tissue or it may mean being in sufficiently close location to sense the electrical signals therefrom or to stimulate the fiber or tissue as discussed previously in connection with FIG. 11. Further, as discussed previously, if the needles are entirely covered with a dielectric and utilize capacitive coupling, the needles do not actually make conductive contact with the body tissue.

If the longitudinal direction of the electrode array is slightly canted with respect to a nerve, electrical contact by some of the needles with some of the nerve fibers is greatly enhanced The spacing and needle length may vary on a given base. In order to reach down into a fissure in the brain, for example, it may be desirable to have longer needles on one portion of the electrode array and shorter needles on another portion. Also, spacing density on one portion of the electrode array may be greater or lesser than on another portion. There may be an abrupt change of needle length or density, or both, in one or more directions. Or there may be a graded or gradual changes in one or more directions.

It is to be understood that the array may be sized to fit the particular application and may be planar, multiplanar, curved, twisted, or other desired shape as required in the particular circumstances involved. Ordinarily, the needles of the electrode array would be disposed on a rigid base. However, it is to be appreciated that the base may be flexible, or that the electrode array may be comprised of needles on a plurality of bases In general, the needles in an array should be held in relatively fixed spacing with respect to each other. It is intended to cover by "relatively fixed" terminology, instances in which the base is flexible, curved, stretchable, etc. Among the suitable bases are silicon, sapphire, or germanium. Numerous ceramics are also suitable for such biomedical use. Biomedical grade plastics may also be used such as the polyamides, polymethacrylate, acrylics, polycarbonates, etc., to the extent that such plastics may be implantable or rendered implantable.

The needles may be arranged in random fashion or ordered in columns and/or rows or other ordered arrangements. The optimum embodiment from the standpoint of orderly electrical connection is an ordered arrangement. One embodiment which may be desired is that in which each electrode (except, of course, those near the edges of the array) is surrounded by six other electrodes, all equidistantly spaced. The needles are electrically connected to a terminal which may, likewise, be randomly located or located in columns and/or rows. The terminal may include bonding pads which provide an electrical connection between the needles and other electrical circuits. Connection points need not be in the same arrangement as the needles. Thus, the needles may be located in columns, but not rows, and the terminals may be located in columns and rows.

It should be understood that the electrode array, as described herein, provides a greater likelihood than the prior art of successfully contacting a desired nerve fiber or desired location in a part of the brain or other part of the body. Through testing and selection of appropriate terminals, needles which have successfully made a desired contact with a particular nerve fiber or target cell can be connected to output equipment for sensing purposes or input equipment for stimulating purposes.

It may be further understood that the electrical parameters which govern the successful application of the electrode array, employed either as a recording electrode or as a stimulating electrode, are the same as the parameters employed for prior art electrodes. For stimulating, the parameters include stimulus rate, wave form, analog or pulsatile type, and amplitude sufficient to depolarize nearby neurons without exceeding the minimum amplitude sufficient to cause electrolysis at the electrode surface. For sensing, the parameters involve the reduction of noise and amplification of signal. These various electrical parameters are discussed in the prior art literature and may be employed for use and operation the electrode arrays disclosed and described herein.

The needles may be constructed as "cones" and a method of construction may use techniques similar to those taught in U.S. Pat. Nos. 3,755,704, 3,789,471, and 3,812,559, each naming Charles A. Spindt et al. as inventors U.S. Pat. No. 3,453,478, naming Kenneth R Soulders and Louis N. Heynick as inventors, also discloses background technology for constructing cones. Of course, it is not essential that the needles be "cones" as described therein, but may be of pyramidal shape or shaped as any sharp protuberance. Further information on the fabrication technology involved, may be found in an article by C. A. Spindt and others, entitled "Physical Properties of Thin-Film Field Emission Cathodes with Molybdenum Cones," Journal of Applied Physics, vol. 47 (12), Dec. 1976. In those patents and the article, the intended use of the structure and method is to provide field emission cathodes and field ionizers. Such needles, as disclosed by Spindt, contemplate electron-emitting structures as may be utilized in a vacuum tube. Also, he contemplates an electric field of megavolts per centimeter and current density of millions of amperes per square centimeter. For electron emission, contemplated voltages are of the order of kilovolts and for field ionization, approximately ten fold higher See Col. 2, 1.3 et seq., Pat. No. 3,812,559.

The device of the invention, on the other hand, as either a sensor or a stimulator, is concerned with very low electrical currents and voltages. The needles of the electrode array of this invention would, ordinarily, not be connected in common, but each needle would provide its individual output, although it is to be understood that groups of needles could be connected together, to provide a common or reinforced output of either stimulation or sensing. Further, in a particular situation, all needles of an array could be connected together to provide a single stimulating output or a single sensing output.

In one contemplated method of manufacture, a common base (substrate) is used in order to mount the needles and to achieve desired deposition. The base may have to be modified to provide the desired isolation of the individual needles or needle groupings. Such original base, as modified, may provide the necessary electrical conductors to convenient terminals of bonding pads for connecting to other electrical circuits.

The various steps of manufacture of the electrical conductors and terminals (bonding pads) may be accomplished by known techniques of chemical or electrical plating, etching, diffusing, sputtering, evaporation or other suitable techniques. This may be accomplished by using photolithographic or photographic techniques, masks, photoresists, etchants, and associated materials, known to those skilled in the microcircuit art.

A suitable mask may be generated by a drawing, followed by a photograph of the drawing, the making of a negative or positive, covering a mask material with a photoresist, exposing the photoresist through the negative or positive, developing it and etching to generate the mask. Fine mesh screens may be readily purchased or a mask may be created as described above, or by other known techniques.

In one embodiment, the steps of manufacture are as follows:

1. A non-conductive substrate, e.g. silicon having a silicon dioxide layer formed thereon, is used. A foil or film of conductive material is affixed thereon, possibly by sputtering, evaporation or other known integrated circuit manufacturing technologies;

2. Using a photoresist and a suitable mask, a pattern of electrical conductors and terminals (bonding pads) is laid out on the conductive material and all the rest of the material is etched or removed. It would be possible to commence with a non-conducting substrate, and using known chemical deposition techniques, lay down a sensitizer in the form of the desired conductive pattern, which would allow subsequent chemical deposition of a conductive metal as the electrical conductors and terminals;

3. After cleansing the article, a glass passivation layer is laid down on the electrical conductors and terminals;

4. Again, a photoresist, a suitable mask, defining the needle sites, and an etchant are used in order to locate the needle sites and to etch through the glass passivating layer, exposing each of the sites for growing a needle on an electrical conductor of the layer below;

5. The same mask or a similar mask having holes therethrough, at the desired needle sites is disposed over the exposed needle sites in registration with such sites, and deposition of the needles is accomplished through such mask by metallic evaporation using, for example, electron beam or resistive element heating, in a high vacuum chamber. The metal deposits on the mask as well as within the hole on the needle site. The size of the hole becomes progressively smaller as metal is deposited atop the mask. The reduction of the size of the hole is precisely correlated with a reduction in the rate of metal deposition within the hole. The reduction of the size of the hole also reduces the target field within the hole upon which the metal is deposited. As a result, the protuberance formed within each hole assumes a tapered shape, e.g. conical, pyramidal, or needle shaped. The evaporating metal used to form the cones (needles) may be platinum, activated iridium, platinum iridium alloy, possibly, rhenium, or other suitable implantable electrode material. It is desired that the cones be made of a conductor which can deliver stimulus current, if stimulating, or sense very small voltages, if sensing, with little or no corrosion. If the mask is a fine mesh screen through which the needles are deposited, the precise size of the holes required for creating the needles may be obtained by placing the mask (covering the device) in a vacuum deposition system and rotating the device about an axis vertical to its surface and depositing, at a grazing incidence, more metal on the screen or mask layer. This can be used to decrease the starting size of the holes to any diameter. Upon arriving at the desired diameter, the needles may be created by orthogonally plating through such narrowed holes as taught in U.S. Pat. No. 3,812,550, referred to above;

6. The mask through which deposition is accomplished is carefully removed, leaving the needles exposed and providing the "bed of nails;"

7. A photoresist, a mask having the pattern of the test points and terminals and an etchant are used to remove the passivating layer over the test points and terminals in order that connection can be made to the array; and 8.a. If it is desired to make a capacitive electrode array, the protuberances must be coated with a passivating or insulating layer. Aluminum oxide ($Al(2)O(3)$) is a preferred composition for the passivating layer and is widely described and employed in the prior art for this purpose; or 8.b. If it is desired to make a conductive electrode array, the focus and specificity of the protuberances can be enhanced by covering the protuberances with a passivating or insulating layer, except for an area of 1–5 square micrometers at the tips. Hence, electrical contact is made only at the tip of the protuberances and the probability of contacting only one cell is enhanced. The protuberances are initially covered over their entire height with a passivating layer, e.g. aluminum oxide (Al(2)O(3)). The passivating layer is then removed from a small area of the tips by exposure to a controlled plasma etch; or 8.c. Alternatively, passivation may be achieved by fabricating the protuberances with self passivating compositions or with a combination of self passivating and non-passivating composition. For example, the first 9/10ths of the height of the protuberances may be fabricated with tantalum, a self passivating composition. The incomplete cone will have a flat top and will form a passivating layer upon exposure to the atmosphere. However, before the passivation layer is allowed for form, the cone is then completed by the deposition of a non-passivating metal, e.g. gold, iridium, platinum, etc. The last 1/10th of the cone will remain conductive.

The above process utilizes various of the manufacturing steps disclosed in the above mentioned article from the Journal of Applied Physics and in the above mentioned patents.

The manufacturing operation may commence with a thin film sandwich of metal on a dielectric (e.g. silicon dioxide on a base of silicon). The conductive and terminal pattern is formed out of the metal layer, by etching away excess metal. Then the needles are deposited through an appropriately patterned mask to coincide with the conductive patterns, as desired. After the needles have been formed, the entire device could be covered with a glass passivating coat, except with needle tips and terminals if they are desired to be left exposed. They could, of course, be exposed later.

In another method, a thin film sandwich is used, having a bottom layer of dielectric, a next layer of metal, then a dielectric and then metal on top of that. The top layer of metal becomes the mask for creating the needles. The thickness of the bottom dielectric layer is determined by what rigidity and strength is necessary in order to hold on to and carry the electrode array. The second dielectric thickness is determined by the spacing desired between the top metal layer (which will form a mask for the needle growing) and the middle metal layer upon which the needles will be grown. A very thin second dielectric layer may be created between the metal layer by the use of evaporated silicon dioxide. The under layer of metal will form the needle sites, the electrical conductors, test points, if any and terminals, (bonding pads, in one embodiment). The top layer of metal is used as a mask for depositing the needle cones on the under layer of metal. This is accomplished by first making holes in the top layer of metal, at intended needle sites, without penetrating the dielectric between the metal layers. This is done by a selective metal etchant (together with a photoresist and a mask) which does not attack the dielectric. Then, an etchant is used to remove the dielectric between the metal layers, at the needle sites. The needles are then "grown" by vacuum evaporation, sputtering or other known techniques.

After having formed the needles on the metal layer on the bottom dielectric layer, all of the second dielectric layer and top metal layer would be removed. The excess metal, not needed for electrical conductors, test points and terminals, of the exposed under layer metal could then be removed. In the alternative the entire underlayer metal could be removed and new metal, making electrical conductors between the needles and terminals could be deposited. The entire electrode array could then be covered with a passivating material, such as silicon dioxide, silicon nitride, aluminum oxide (Al(2)O(3)) or other biocompatible dielectric, and then selectively etched at the terminals, if desired and at the needle points.

If the substrate is silicon or germanium or the like, the electrical conductors and, if desired, switches, multiplexors, amplifiers and other electronic circuits may be provided by doping selected portions of the substrate or by other commonly used techniques. Electrical conductors may be created on the surface of the semiconductor material, in it, or through it, to the opposite side from the protuberances.

In obtaining registration or indexing of masks, covers, or other items, which must be aligned with the array, one or more groups of three cones or needles could be grown in two or more places on the array and a registering cone or needle grown on the other item to be aligned. A needle on the overlying device fits into the space within the group on the other device, as previously described in connection with FIGS. 14 and 15. Of course, the overlaying device may have the groups of needles and the base have the single registering needles. Further, both devices may have a group which fits into a group on the other device.

The materials used in the structure must be biocompatible and suitable for use in or in connection with the living body. It is understood, of course, that certain materials which are not considered biocompatible could be rendered suitable by being treated or covered with a biocompatible material. Thus, glass passivation (covering with glass), oxidation of certain materials, the coating or depositing of biocompatible materials (such as, but not limited to, silicone rubber, certain metals and ceramics or one of the many plastics which are used in the body) may be used to provide a final product which is biocompatible and may be implanted. The electrode or needle material may be platinum, activated iridium, a platinum iridium alloy, a conductive polymer, carbon or other suitable electrically conductive material known by those skilled in the art as suitable for use in connection with the body. In general, metals or other conductive substances which are inert and are least subject to corrosion are used. In the case of stimulating devices, conductive materials which can handle the necessary current densities are required.

In view of the above discussion, it may be understood that the electrode array would be useful in stimulating a gland or a nerve to or in the gland to cause the gland to be active or more active. The electrode array may be used to cause hormonal secretions.

Other uses of a stimulating electrode array or a plurality of electrode arrays would include stimulation of a group of muscles or successive stimulation of groups or portions of a group in order to achieve a desired muscular coordination. Such electrode array may be applied directly to or in the muscle or it may be applied to or in selected nerves (or the central or peripheral nervous system) to provide signals to the muscle. Also, a number of such electrode array may be applied at different locations and their stimulation or sensing coordinated to achieve desired results.

One stimulation application of the electrode array or a plurality of such electrode arrays is in excitation of the brain to provide a sensory response, e.g. vision. The electrode array and its numerous needles may be disposed in the visuosensory and visuopsychic areas of the brain, which involve several kinds of cells. The electrode array may be disposed along the optic nerve or the paths where the optic nerve enters the cortex. The array may be attached to the cortex with the needles penetrating the brain rather than the optic nerve.

The concept of the invention in one of its more important aspects provides for electrical access to the individual elements of a tissue in order to determine which element or elements and its associated needle or needles are useful for the intended purpose. One or more needle outputs may be found to be useful in the particular application involved.

It should also be appreciated that, as taught hereinabove, the device may be untethered, through one or more means for transmitting information, receiving information or receiving power.

Although the invention has been described and illustrated in detail, it is to be clearly understood that the same is by way of illustration and example only and is not to be taken by way of limitation, the spirit and scope of this invention being limited only by the terms of the appended claims.

What is claimed is:

1. An electrode array for establishing electrical contact with tissue of a living body, the electrode array comprising:
   a base having a support surface,
   a plurality of electrically conductive protuberances extending substantially perpendicular to and from said support surface of said base in a two dimensional array, each of said protuberances having a tip for electrically contacting the tissue,
   a plurality of conductors incorporated onto said base and electrically connected to said protuberances for conducting electric signals to or from said protuberances, and
   a dielectric coat covering and electrically insulating said protuberances, exclusive of the tips.

2. An electrode array as described in claim 1 wherein:
   said protuberances perpendicularly extend from said base with a range of heights from approximately 0.5 micrometers to on the order of 100 micrometers.

3. An electrode array as described in claim 1 wherein:
   said protuberances are adjacently spaced with a range from approximately 0.5 micrometers to on the order of 100 micrometers upon said base.

4. An electrode array as described in claim 1 for establishing an array of electrical contacts with tissue, wherein:
   each conductor is electrically connected to at least one of said protuberances for forming a two dimensional array, whereby each tip is capable of establishing an electrical contact with the tissue and the two dimensional array of said protuberances is capable of establishing an array of electrical contacts with the tissue.

5. An electrode array as described in claim 4 further comprising:
   a plurality of means for generating a signal,
   each of said generating means being electronically coupled to one of said conductors.

6. An electrode array as described in claim 4 further comprising:
   means for analyzing a plurality of signals,
   said analyzing means being electronically coupled to each of said conductors.

7. An electrode array as described in claim 4 wherein:
   said protuberances perpendicularly extend from said base with a range of heights from approximately 0.5 micrometers to on the order of 100 micrometers, and
   said protuberances are adjacently spaced with a range from approximately 0.5 micrometers to on the order of 100 micrometers upon said base.

8. An electrode array as described in claim 4 wherein the electrode array electrically contacts individual cellular components of the tissue of the living body and wherein:
   each tip of said protuberances is sufficiently small and sharp to be capable of making electrical contact with a single cellular component within the tissue.

9. An electrode array as described in claim 4 wherein:
   said dielectric coat has a biocompatible composition for rendering the electrode array implantable into the living body.

10. A capacitor electrode array for capacitively coupling with the tissue of a living body, the capacitor electrode array comprising:
    a base having a support surface,
    a plurality of electrically conductive protuberances extending substantially perpendicular to and from said support surface of said base in a two dimensional array, each of said protuberances having a tip,
    a dielectric coat covering said protuberances for capacitively coupling each of said protuberances with the tissue, and
    a plurality of conductors incorporated onto said base and electrically connected to said protuberances for conducting electric signals to or from said protuberances.

11. A capacitor electrode array as described in claim 10 wherein:
    said protuberances perpendicularly extend from said base with a range of heights from approximately 0.5 micrometers to on the order of 100 micrometers.

12. A capacitor electrode array as described in claim 10 wherein:
    said protuberances are adjacently spaced with a range from approximately 0.5 micrometers to on the order of 100 micrometers upon said base.

13. A capacitor electrode array as described in claim 10 wherein:
    said protuberances perpendicularly extend from said base with a range of heights from approximately 0.5 micrometers to on the order of 100 micrometers and
    said protuberances are adjacently spaced with a range from approximately 0.5 micrometers to on the order of 100 micrometers upon said base.

14. A capacitor electrode array as described in claim 10 further comprising:
    means for generating multiple electric signals,
    said generating means being electronically coupled to said conductors.

15. A capacitor electrode array as described in claim 10 further comprising:
   means for analyzing multiple electrical signals,
   said analyzing means being electronically coupled to said conductors.

16. A combination of two electrode arrays for establishing electrical contact with a nerve, the combination comprising:
   a first electrode array including a first base, a first array of electrically conductive protuberances supported by said first base, and a first set of conductors connected to the first array of protuberances,
   a second electrode array including a second base, a second array of electrically conductive protuberances supported by said second base, and a second set of conductors connected to the second array of protuberances, and
   cooperative means extending from the first and second bases for indexing and aligning the first electrode array opposite the second electrode array with the nerve sandwiched between the first and second electrode arrays and with the first and second array of protuberances penetrating and contacting the nerve.

17. A combination of two electrode arrays for capacitively coupling with a nerve, the combination comprising:
   a first capacitor electrode array including a first base, a first array of electrically capacitive protuberances having a dielectric coat supported by the first base, and a first set of conductors connected to the first array of protuberances,
   a second capacitor electrode array including a second base, a second array of electrically capacitive protuberances having a dielectric coat supported by the second base, and a second set of conductors connected to the second array of protuberances, and
   cooperative means extending from the first and second bases for indexing and aligning the first capacitor electrode array opposite the second capacitor electrode array with the nerve sandwiched between the first and second capacitor electrode arrays and with the first and second array of capacitive protuberances penetrating and capacitively coupling with the nerve.

18. A method for establishing electrical contact with a nerve from a living body, the method comprising the following steps:
   step (a): contacting the nerve with a combination of two electrode arrays including a first electrode array, a second electrode array, and indexing means,
   the first electrode array including a first base, a first array of electrically conductive protuberances supported by the first base, and a first set of conductors connected to the first array of protuberances,
   the second electrode array including a second base, a second array of electrically conductive protuberances supported by the second base, and a second set of conductors connected to the second array of protuberances, and
   the indexing means extending from the first and second bases for indexing and aligning the first electrode array opposite the second electrode array with the nerve sandwiched between the first and second electrode arrays and with the first and second array of protuberances penetrating and contacting the nerve, and
   step (b): connecting both the first and second set of conductors of each electrode array with electrical circuits.

19. A method for capacitively coupling to a nerve from a living body, the method comprising the following steps:
   step (a): contacting the nerve with a combination of two capacitive electrode arrays including a first capacitive electrode array, a second capacitive electrode array, and indexing means,
   the first capacitive electrode array including a first base, a first array of electrically conductive protuberances supported by the first base, and a first set of conductors connected to the first array of protuberances, and
   the second capacitive electrode array including a second base, a second array of electrically conductive protuberances supported by the second base, and a second set of conductors connected to the second array of protuberances, and
   the indexing means for indexing and aligning the first capacitive electrode array opposite the second capacitive electrode array with the nerve sandwiched between the first and second capacitive electrode arrays and with the first and second arrays of protuberances penetrating and capacitively coupling with the nerve, and
   step (b): connecting both the first and second set of conductors of each electrode array with electrical circuits.

20. A method for making an electrode array comprising the steps of:
   (a) obtaining a base with a non-conductive surface;
   (b) depositing a layer of electrically conductive material atop the non-conductive surface;
   (c) forming conductors on the base by partially removing the layer of electrically conductive material;
   (d) defining sites upon the conductors for an array of protuberances;
   (e) depositing electrically conductive protuberances upon the sites for the array; and
   (f) forming a dielectric coat upon the protuberances.

* * * * *